(12) United States Patent
Ueno

(10) Patent No.: US 9,393,392 B2
(45) Date of Patent: Jul. 19, 2016

(54) POULTICE APPLICATOR

(71) Applicant: SANFREUND CORPORATION, Tokyo (JP)

(72) Inventor: Hideo Ueno, Tokyo (JP)

(73) Assignee: Sanfreud Corporation, Tokyo (JP)

( * ) Notice: Subject to any disclaimer, the term of this patent is extended or adjusted under 35 U.S.C. 154(b) by 325 days.

(21) Appl. No.: 14/027,677

(22) Filed: Sep. 16, 2013

(65) Prior Publication Data

US 2014/0227020 A1    Aug. 14, 2014

(30) Foreign Application Priority Data

Sep. 18, 2012   (JP) .................................. 2012-204989

(51) Int. Cl.
*A61M 35/00*      (2006.01)
*A61F 13/40*      (2006.01)

(52) U.S. Cl.
CPC ........... *A61M 35/003* (2013.01); *A61M 35/006* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,937,910 A | * | 7/1990 | Frazier | ................... B43L 21/00 15/230.17 |
| 6,810,554 B2 | * | 11/2004 | McKay | ................... A47L 13/18 15/104.002 |
| 2014/0007906 A1 | * | 1/2014 | Bates | ...................... A47L 13/24 134/6 |

FOREIGN PATENT DOCUMENTS

JP    8-310962    11/1996

* cited by examiner

*Primary Examiner* — David Walczak
(74) *Attorney, Agent, or Firm* — Jordan and Koda PLLC

(57) ABSTRACT

A poultice applicator in which a plurality of disposable rubber sponges, cloths or resins are attached to the poultice applicator in advance, used rubber sponges, cloths or resins are removed sequentially, and unused rubber sponges, cloths or resins are used to apply a drug to skin. For example, an analgesic and antiphlogistic poultice and/or the antipruritic and anti-inflammatory poultice may be contained in a poultice applicator in which a plurality of disposable rubber sponges, cloths or resins are attached to the existing rubber sponge, cloth or resin.

2 Claims, 17 Drawing Sheets

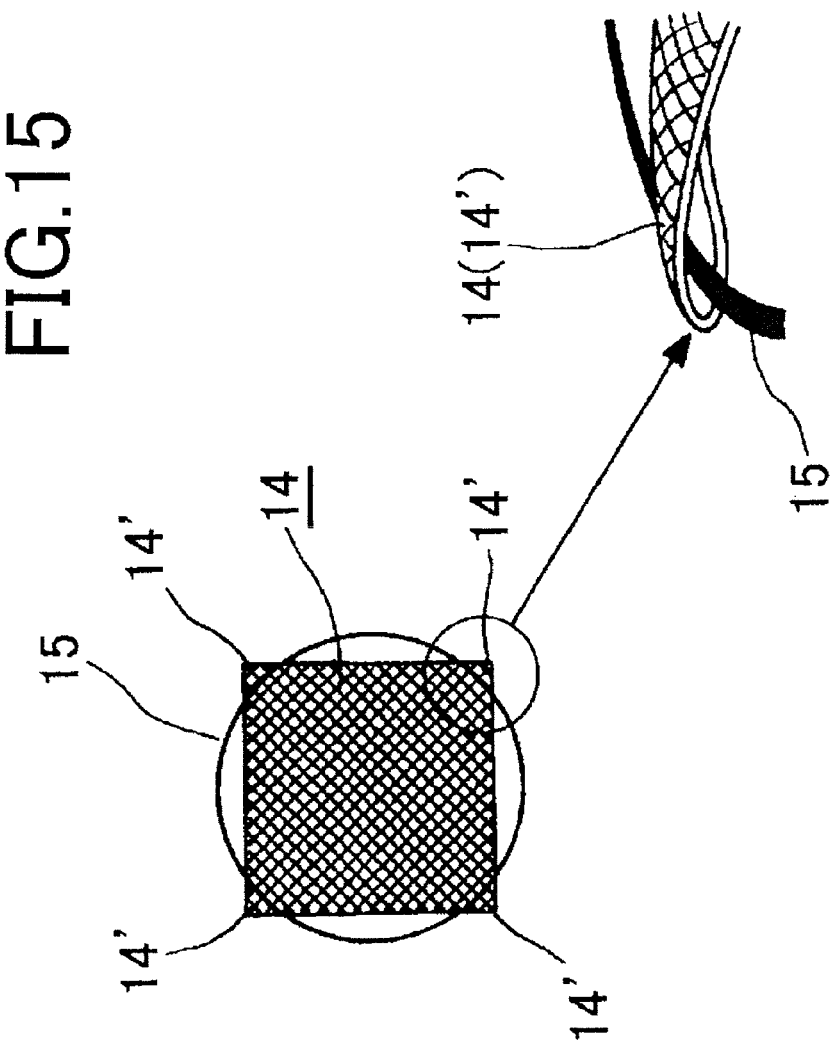

POULTICE APPLICATOR

BACKGROUND OF THE INVENTION

The present invention relates to a poultice applicator, and a replacement rubber sponge, cloth, or resin of the poultice applicator to which a plurality of disposal exchange members for using analgesic and antiphlogistic poultice that relieves the pain of low back pain, etc., antipruritic and anti-inflammatory poultice that stops itching insect bites.

Today, in order to relieve the symptoms such as stiff shoulder, back pain, joint pain, and bruises, analgesic and antiphlogistic poultice can be used. Further, in order to stop itching insect bites, antipruritic and anti-inflammatory poultice.

For example, the analgesic and antiphlogistic poultice and/or the antipruritic and anti-inflammatory poultice may be contained in a poultice applicator that may be made of glass, plastic or the like, and a rubber sponge is attached to an application member (application mouse) of the poultice applicator includes. As a method for using the poultice applicator, direct application to the affected area is usually adopted. That is, the rubber sponge attached to the end of the poultice applicator is applied to skin directly, and the container is pressed to exude and apply a poultice through a rubber sponge to the skin.

However, when using the poultice applicator, as mentioned above, the rubber sponge is used to apply the poultice to the affected area directly. For this reason, there is a case where some people dislike the use of rubber sponge that others have used.

A Japanese Patent Laid-Open Publication (08-310962) has been published. This Japanese patent laid-open publication discloses a poultice whose effect has high permeability of the skin is strong, excellent immediate effect of analgesic, and anti-inflammatory such as antipyretic, analgesic, and anti-inflammatory, antipyretic in a very short time.

SUMMARY OF THE INVENTION

In order to solve the above mentioned problems, it is provided a poultice applicator, and a replacement rubber sponge, cloth, or resin of the poultice applicator to which a plurality of disposable rubber sponges is attached in advance such that rubber sponge used may be removed sequentially from the poultice applicator and new rubber sponge may be used to apply the poultice to skin.

According to the present invention, it is provided a poultice applicator in which poultice to be applied to human skin is contained and an existing rubber sponge, cloth, or resin of the poultice applicator, the existing rubber sponge, cloth, or resin of the poultice applicator is covered by a plurality of disposal rubber sponge, cloth, or resin of the poultice applicator.

Further, the existing rubber sponge, cloth, or resin of the poultice applicator is configured to be attached to the end of the disposable member attachment portion, and a plurality of disposable rubber sponge, cloth, or resin covers the existing rubber sponge, cloth, or resin sequentially, and attached to the disposable member attachment portion, for example, by press-fitting using a fastener.

Further, the disposable rubber sponge, or cloth, or a resin may be a mesh sheet having, for example, four corners, at which the disposable rubber sponge, or cloth, or a resin may be fixed to a fastener having a shape of rubber-band, the fastener is fitted into the groove of the disposable member attachment portion such that the disposable rubber sponge, or cloth, or a resin may be secured to the disposable member attachment portion by an elastic force, e.g., that of the fastener.

According to the present invention, it is provided the disposable member that includes a mesh part that is formed in the middle and has a predetermined size, a perforations that is formed on the outside of the mesh portion, a projection that is formed between the mesh part and the perforations, and a skirt portion that is positioned outside of the perforations, and after the disposable member is attached to the poultice applicator using the projection, the mesh portion may be separated from the disposable member along the perforations.

According to the present invention, it is provided the disposable member that includes a mesh part that is formed in the middle and has a predetermined size, a notch that is a predetermined length formed along the diameter direction of the mesh, and a bottom portion that is positioned outside of the mesh, and after the disposable member is attached to the poultice applicator using the notch, the mesh part may be cut and opened along the notch.

BRIEF DESCRIPTION OF THE DRAWINGS

FIG. 15 is a diagram illustrating a configuration of disposable rubber sponge that is used in fifth embodiment;

DESCRIPTION OF THE PREFERRED EMBODIMENTS

Embodiments of the present invention will be described below in detail with reference to the drawings.

First Embodiment

Figure 1:
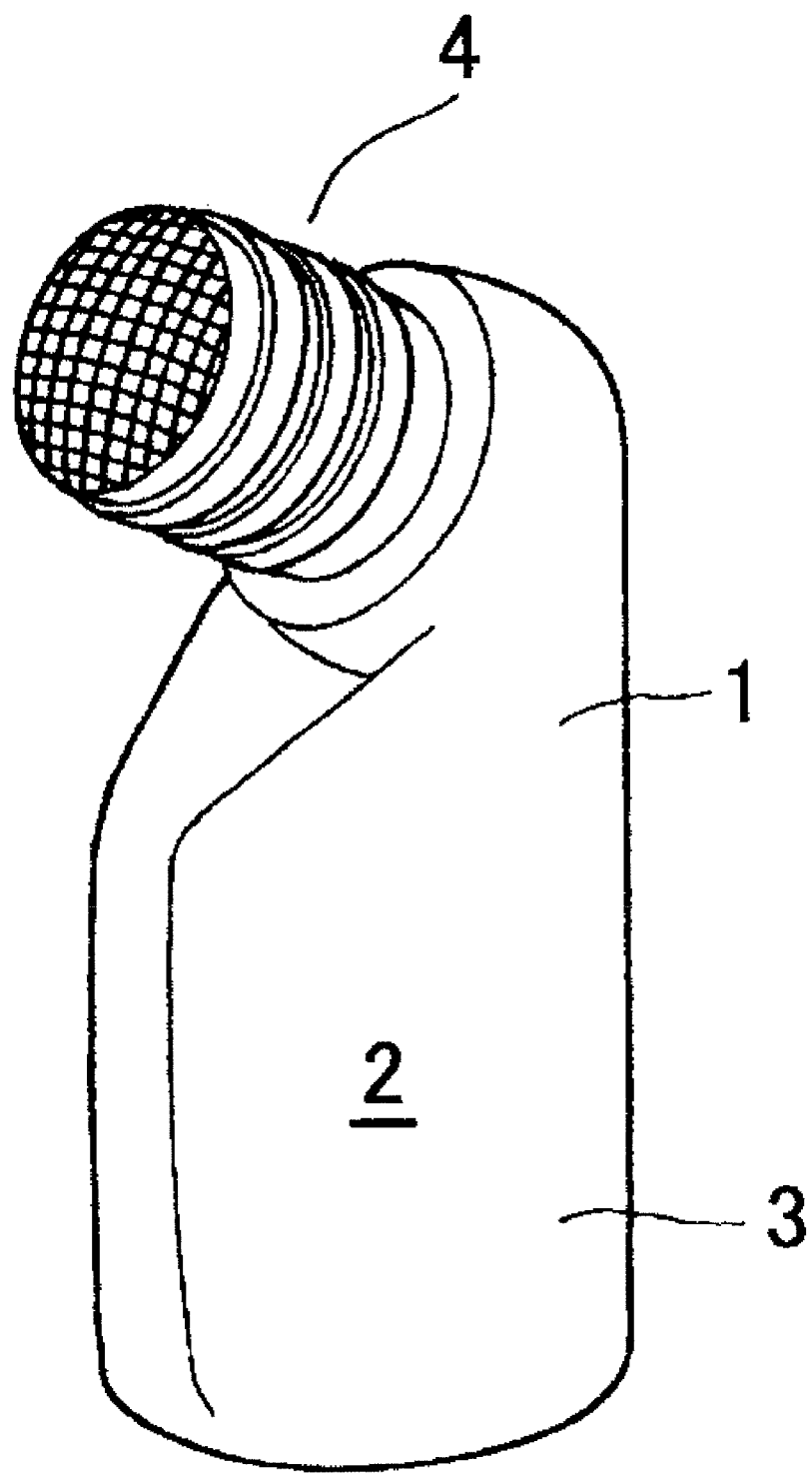
FIG. 1 is an external view of a poultice applicator to which a disposable rubber sponge is attached and in which analgesic and antiphlogistic poultice is contained.

FIG. 1 is a diagram illustrating an example of a poultice applicator 1, which is formed as a plastic container, to which a disposable rubber sponge according to the present embodiment is attached and in which analgesic and antiphlogistic poultice 2 is contained. Further, the poultice applicator 1 may be configured to accommodate the anti-inflammatory anti-pruritic poultice instead of the analgesic and antiphlogistic poultice.

In FIG. 1, the poultice applicator 1 includes a housing portion 3 in which the analgesic and antiphlogistic poultice 2 may be contained and a rubber sponge attachment portion 4. Further, three disposable rubber sponges (e.g., rubber sponge sheets) are attached to the rubber sponge attachment portion 4, as to be mentioned below, and the analgesic and antiphlogistic poultice 2 may be discharged through the disposable rubber sponges and an existing rubber sponge. As shown in FIG. 1, the rubber sponge attachment portion 4 may be configured to be projected obliquely upward with respect to housing part 3 of the poultice applicator (the plastic container) 1.

Figure 2:
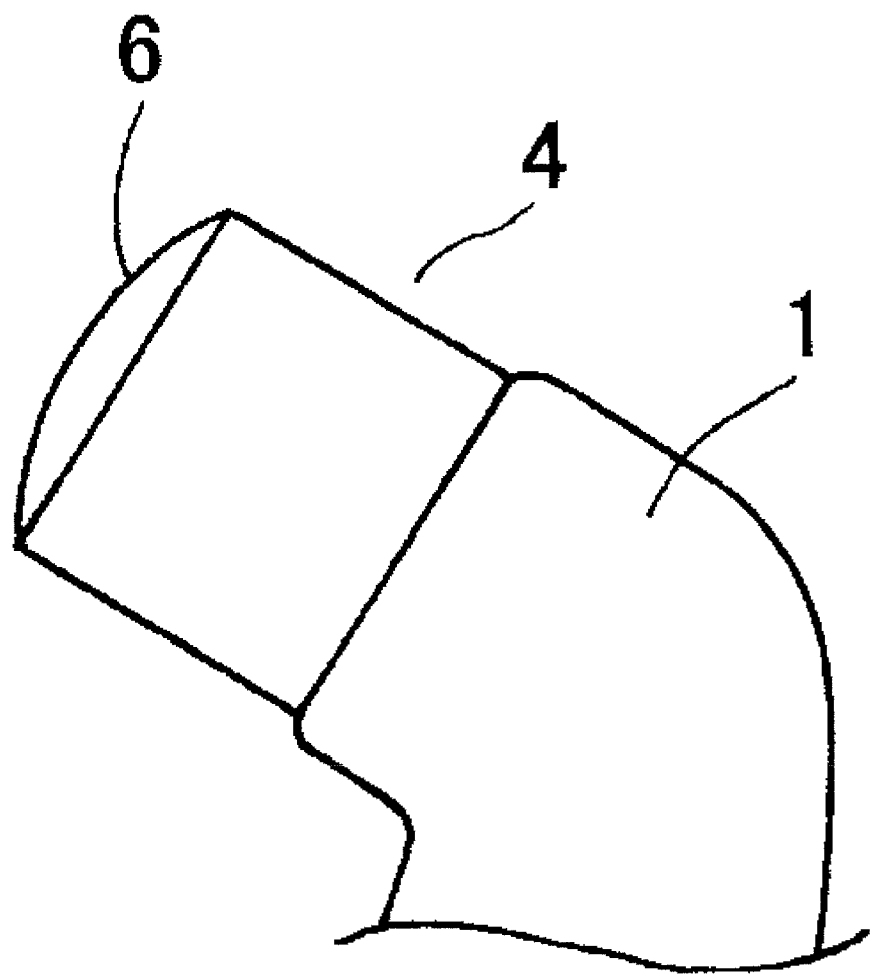
FIG. 2 is a diagram illustrating a configuration of a sponge rubber attachment portion of the first embodiment.

Next, a configuration of the rubber sponge attachment portion 4 will be explained. FIG. 2 is a diagram illustrating the configuration of a sponge rubber attachment portion 4, wherein the disposable rubber sponge is not provided (covered). The existing rubber sponge 6 is attached to the end of the rubber sponge attachment portion 4, and the three disposable rubber sponges 5a, 5b, 5c are arranged sequentially over the existing rubber sponge 6.

Figure 3:
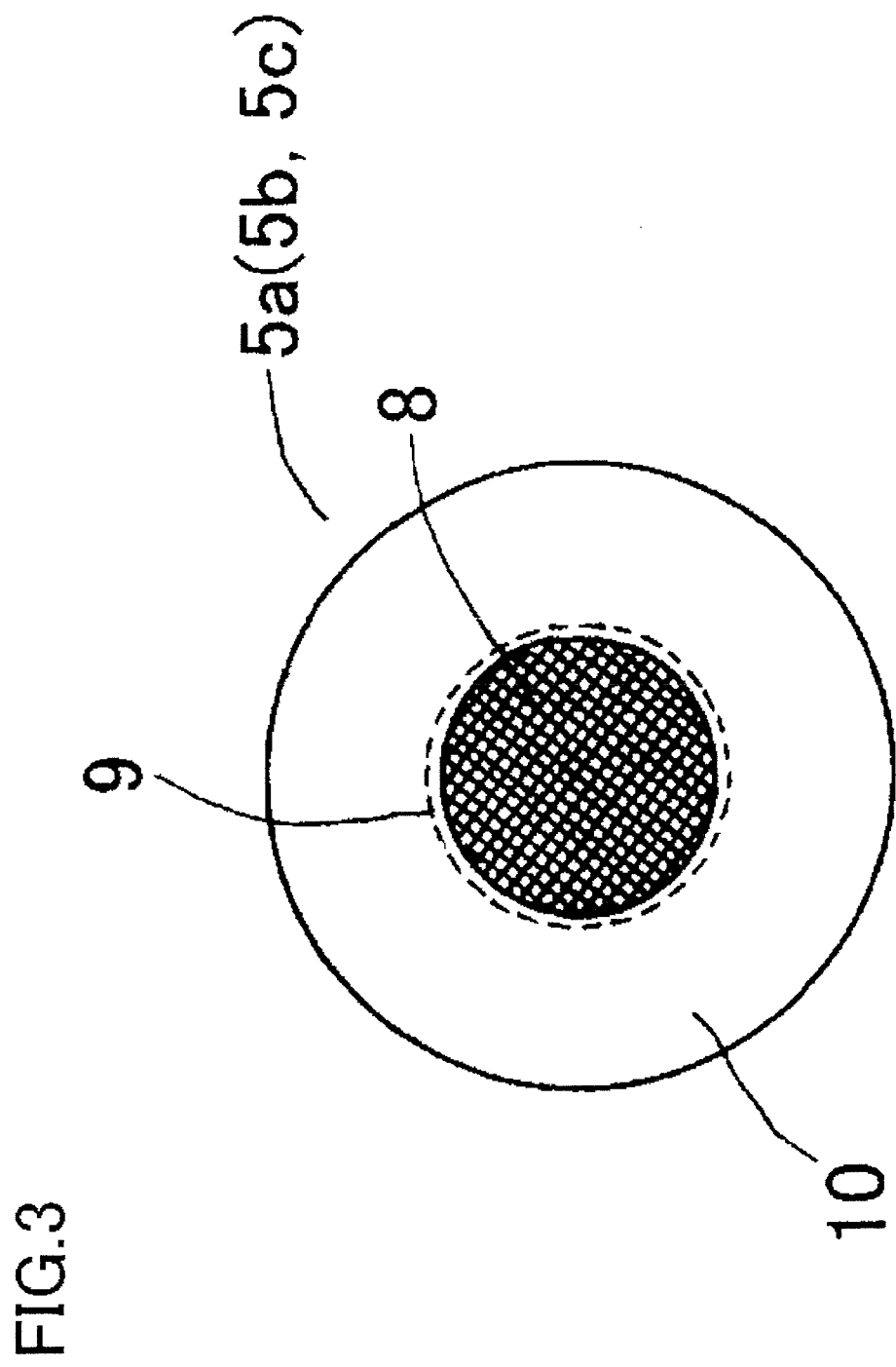
FIG. 3 is a diagram illustrating an example of a disposable rubber sponge.

FIG. 3 illustrates example of the disposable rubber sponges 5a, 5b, 5c, that includes a mesh portion 8 having a predetermined size at the center of the disposable rubber sponge. When the container is pressed, drug in the container may be exuded through the mesh portion 8 that has a white folding along the line indicated by the dotted line 9, for example. Further, a skirt portion 10 of the disposable rubber sponges 5a, 5b, 5c is fixed to the rubber sponge attachment portion 4 by a fastener which will be described below, and may have different sizes depending on the disposable rubber sponges 5a, 5b, 5c.

Figure 4:
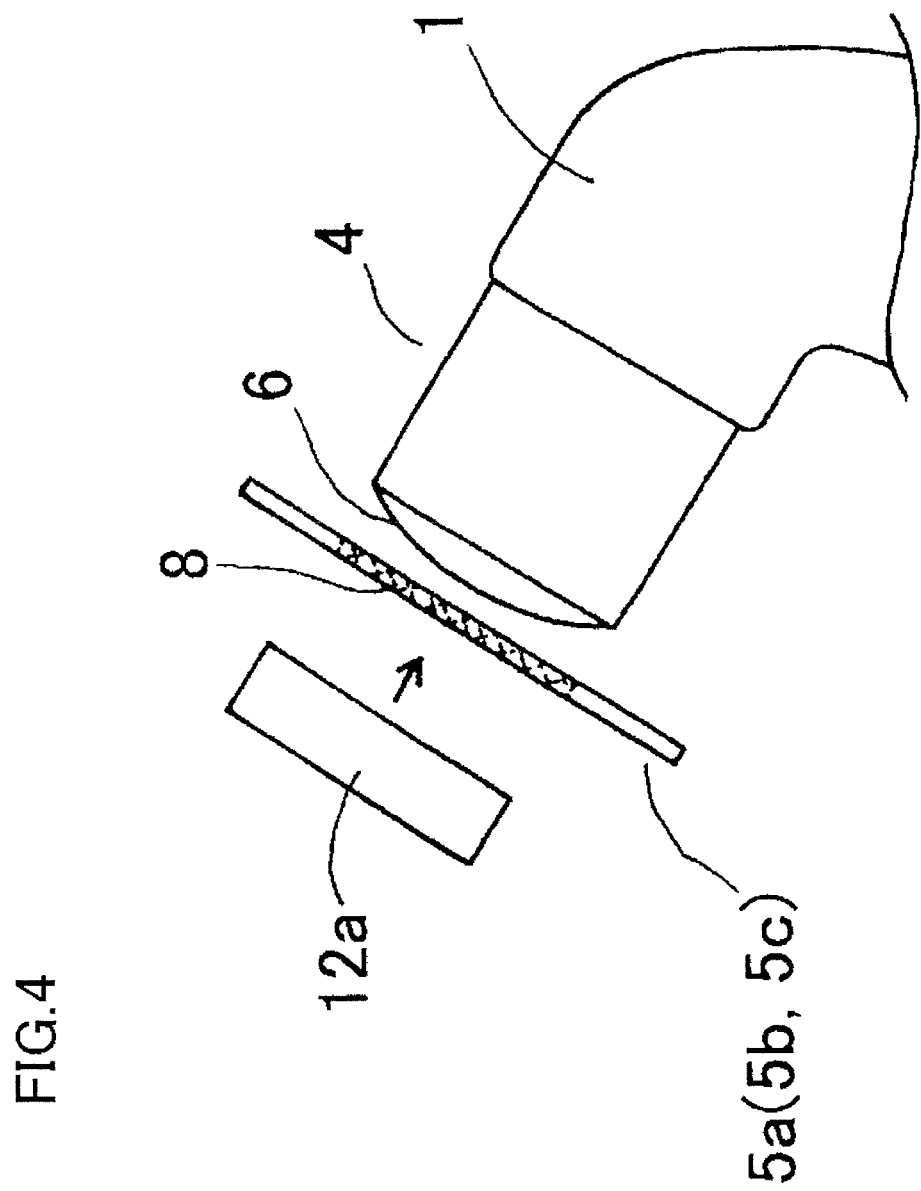
FIG. 4 is a diagram illustrating an example of attaching the rubber sponge attachment portion to the disposable rubber sponge.

FIG. 4 is a diagram illustrating an example of attaching the rubber sponge attachment portion 4 to the disposable rubber sponges 5a, 5b, 5c. As mentioned above, the existing rubber sponge 6 is attached to the end of the rubber sponge attachment portion 4, and, in the poultice applicator 1 according to the present embodiment, the existing rubber sponge 6 is covered by the disposable rubber sponges 5a, 5b, 5c.

Figure 5:
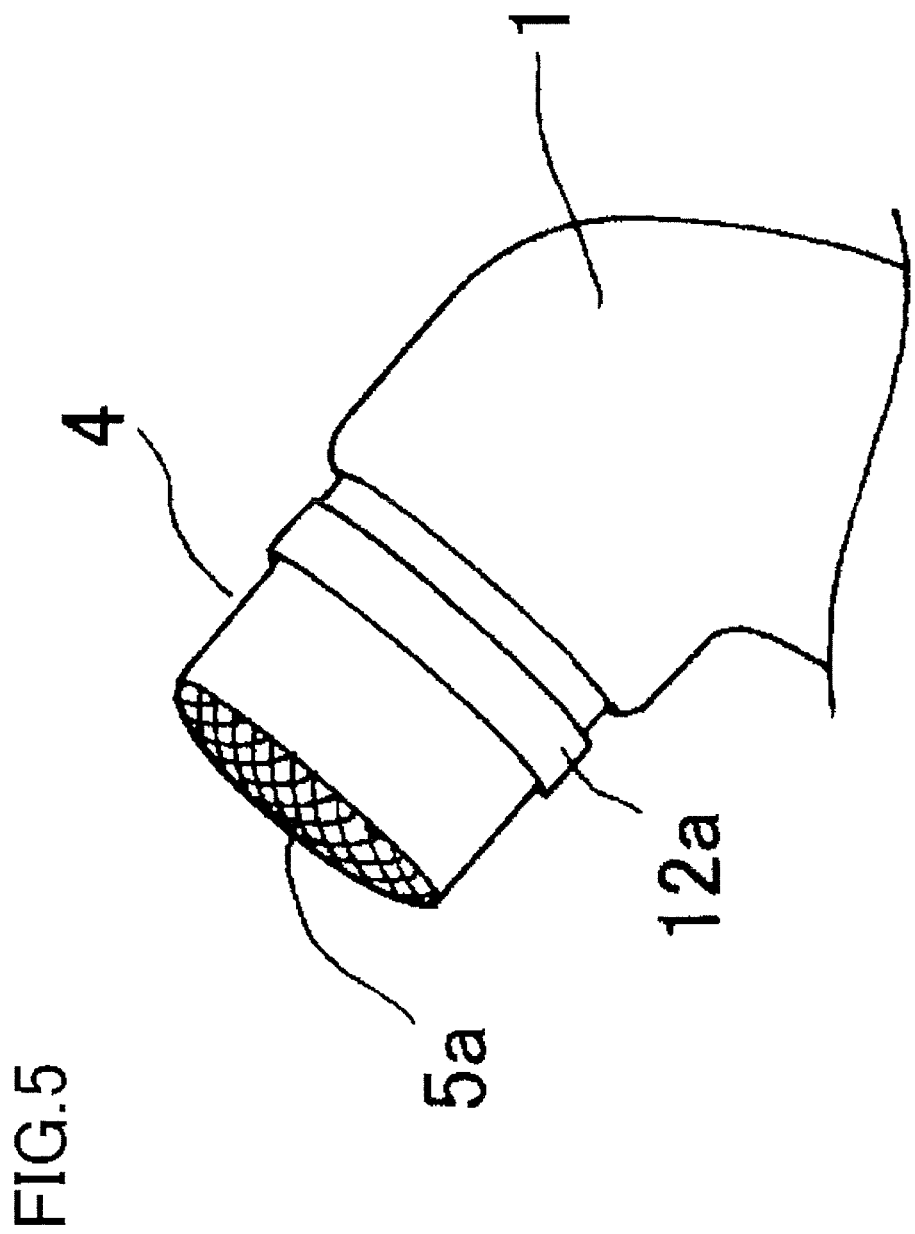
FIG. 5 is a diagram illustrating a state in which a first disposable rubber sponge is provided to cover the rubber sponge attachment portion by a fastener.

Specifically, the first disposable rubber sponge 5a covers the existing rubber sponge 6 and the existing rubber sponge 6 is attached to the rubber sponge attachment portion 4 by the fastener 12a. In other words, as shown in FIG. 4, the fastener 12a is press-fitted toward the direction illustrated by the arrow to cover the existing rubber sponge 6 that is provided at the end of the rubber sponge attachment portion 4, and hence the disposable rubber sponge 5a is attached to the rubber sponge attachment portion 4. Further, FIG. 5 is a diagram illustrating a state in which the first disposable rubber sponge 5a is provided to cover the rubber sponge attachment portion 4 by the fastener 12a.

Figure 6:
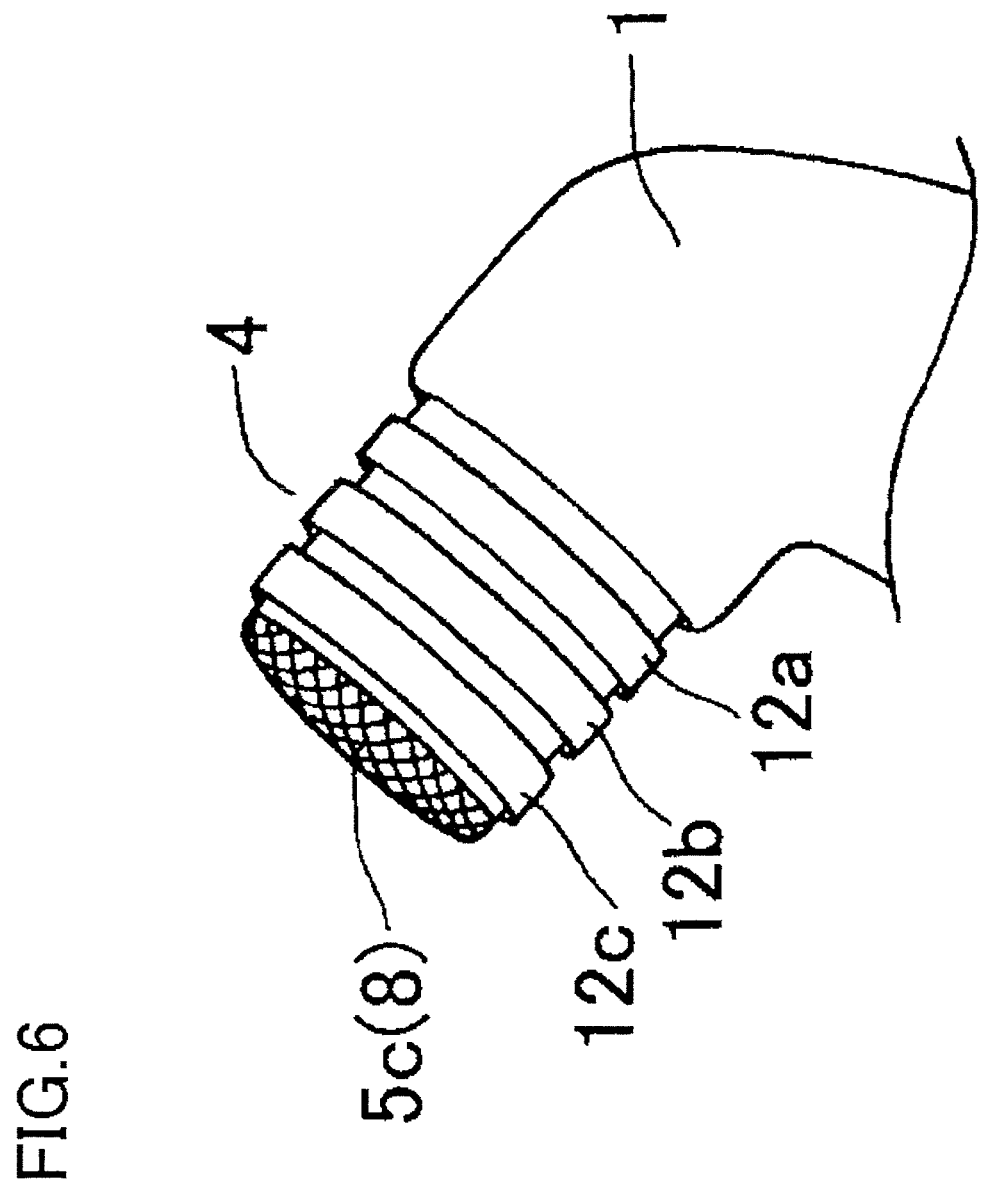
FIG. 6 is a diagram illustrating a state in which three disposable rubber sponge sheets are provided to cover the rubber sponge attachment portion.

In the same way, the disposable rubber sponges 5b, 5c, are attached to the rubber sponge attachment portion 4. FIG. 6 is a diagram illustrating a state in which the three disposable rubber sponges 5a, 5b, 5c are provided to cover the rubber sponge attachment portion 4. That is, the disposable rubber sponge 5b is attached to the rubber sponge attachment portion 4 by the fastener 12b, and the disposable rubber sponge 5c is attached to the rubber sponge attachment portion 4 by the fastener 12c.

Thus, as shown in FIG. 6, the mesh 8 that is provided at the end of the rubber sponge attachment portion 4 is the disposable rubber sponge 5c, and the disposable rubber sponges 5b, 5a, and further the existing rubber sponge 6 are positioned under the disposable rubber sponge 5c.

Therefore, when using the poultice applicator 1 of the present embodiment, the disposable rubber sponge 5c attached to the top of the four rubber sponge attachment portion is first used, then the fastener 12c is removed by a user such that the disposable rubber sponge 5c that is positioned at the top level is discarded, and the disposable rubber sponge 5c that is positioned at the top level is used to apply the drug to the skin.

By using in this way, it is possible to prevent from using a rubber sponge touched to the skin of another person, and from pausing on use of the poultice applicator.

Further, even when applying drug to their skin by using the same poultice applicator 1 later, it is possible to apply the drug to their skin by using the new disposable rubber sponge 5c. Hence, the poultice applicator 1 is very effective.

Further, although the embodiment described above discloses the poultice applicator 1 includes the three disposable rubber sponges 5a, 5b, 5c, it may not to be limited. It is possible that the poultice applicator 1 includes the three or more disposable rubber sponges.

Figure 7:
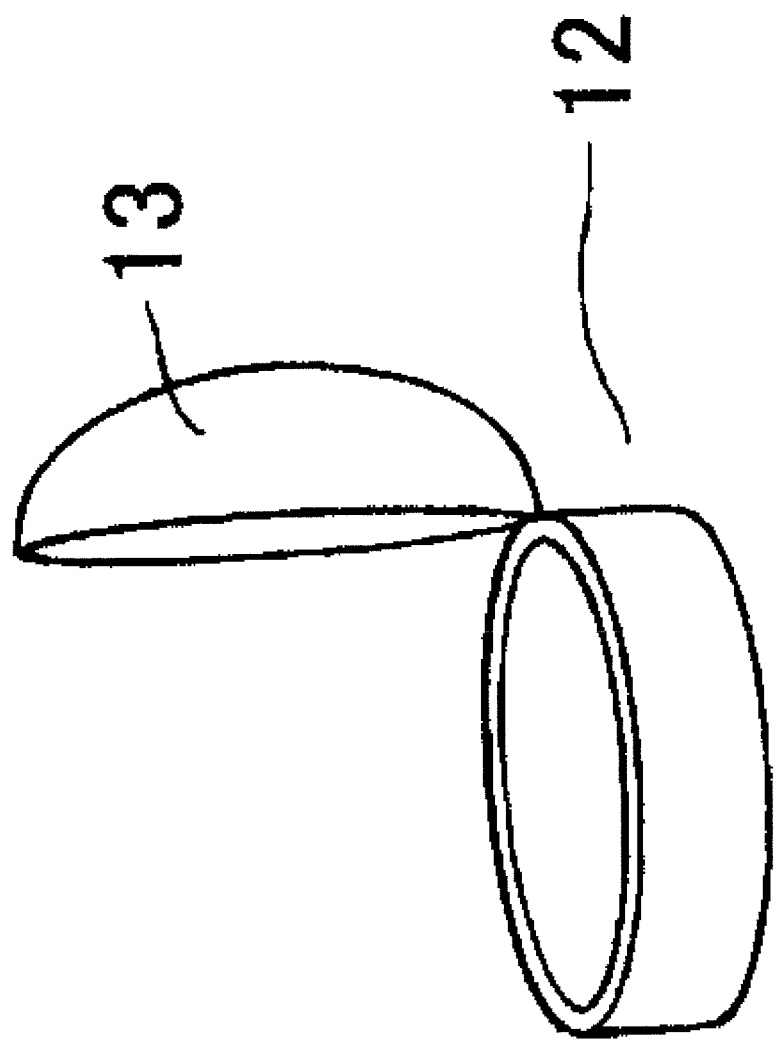
FIG. 7 is a diagram illustrating an example of a fastener with a lid.
Figure 8:
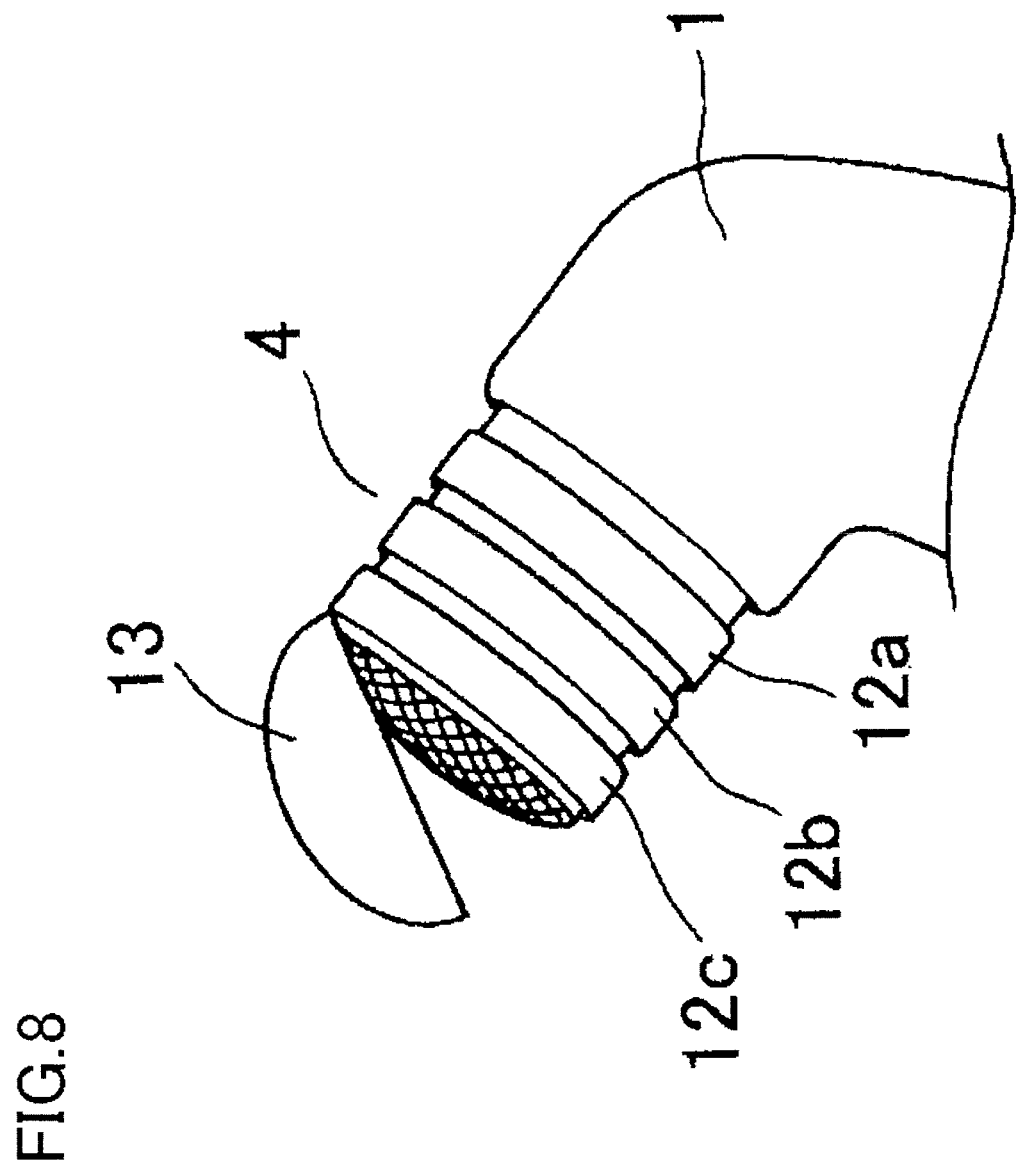
FIG. 8 is a diagram illustrating a state in which the rubber sponge is attached to the attachment portion to cover the fastener.

Further, it may be configured to use the fastener 12 to which the cover 13 shown in FIG. 7 is attached. Such a configuration may lead to the poultice applicator 1 shown in FIG. 8, in which the disposable rubber sponge positioned at the top level is fixed by the fastener with a lid 12 thereby obtaining effectiveness in hygiene.

According to the present invention, it is provided the poultice applicator, and the replacement rubber sponge, cloth, or resin of the poultice applicator. Using the poultice applicator, when the other person uses the poultice applicator, it is possible to remove the used rubber sponge, apply drug to the skin using the new rubber sponge, and hence, no hygienic problems may be occurred even if used among people, lending and borrowing may be possible without hesitation.

Second Embodiment

Next, a second embodiment according to the present invention will be explained.

In the description of the first embodiment, each of the disposable rubber sponges is fixed by a corresponding fastener. However, in the present embodiment, each of the disposable rubber sponges is configured to have a perforations, and a plurality of the disposable rubber sponges are fixed by a single fastener. And using the poultice applicator, the perforations may be used to remove used rubber sponge sequentially. In the following, it will be explained in detail.

Figure 9A:
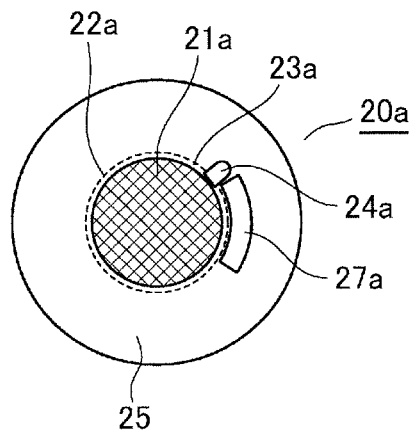
FIGS. 9A~9E are diagrams for explaining an example of a disposable rubber sponge to be used in the second embodiment.

FIG. 9A is a diagram for explaining an example of a disposable rubber sponge 20a to be used in the present embodiment. In this embodiment, the disposable rubber sponge 20a includes a mesh portion 21a having a predetermined size at the middle, through which drug contained in the poultice applicator is exuded when the container is pressed. Further, perforations 22a having the circular shape is formed outside of the mesh portion 21a. Furthermore, the projection 24a is formed in the rubber sponge portion 23a between the perforations 22a and the mesh portion 21a, by picking the projection 24a, for example, pulling up the projections 24a, the mesh portion 21a can be cut along the perforations 22a. Further, the skirt portion 25 outside of the perforations 22a is formed of a rubber sponge shown in FIG. 9A.

The opening 27a formed on the outside of the perforations 22a is configured to expose projections 24b-24e of the rubber sponge 20b-20e to the outside, as to be described later.

Figure 9B:
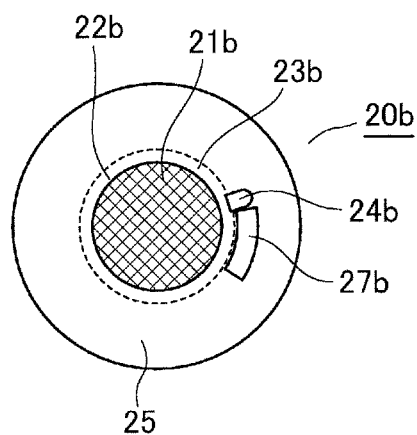

Similarly, FIG. 9B is a diagram for explaining an example of a disposable rubber sponge 20b to be used in the present embodiment. In this embodiment, the disposable rubber sponge 20a includes a mesh portion 21b having a predetermined size at the middle, a circular perforations 22b is formed outside the mesh portion 21b, and a projection 24b is formed at a rubber sponge portion 23b formed between the mesh portion 21b and the circular perforations 22b. However, in the case of the disposable rubber sponge 20b, the perforations 22b outside of the mesh portion 21b is formed outside the perforations 22a of the disposable rubber sponge 20a.

The opening 27b formed on the outside of the perforations 22b is configured to expose the projections 24c-24e to be described later of the rubber sponge 20c-20e.

Figure 9C:
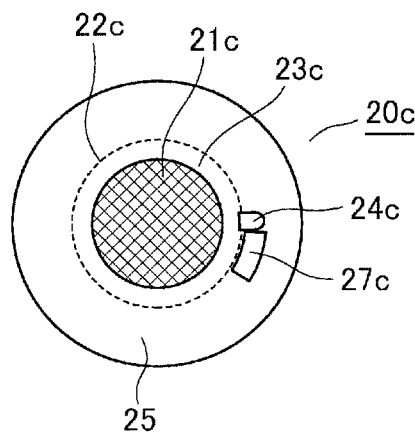

Similarly, FIG. 9C is a diagram for explaining an example of a disposable rubber sponge 20c to be used in the present embodiment. In this embodiment, the disposable rubber sponge 20c includes a mesh portion 21c having a predetermined size at the middle, a circular perforations 22c is formed outside the mesh portion 21c, and a projection 24c is formed at a rubber sponge portion 23b formed between the mesh portion 21b and the circular perforations 22c, wherein the circular perforations 22c outside of the mesh portion 21c is positioned outside a position of the perforations 22b of the disposable rubber sponge 20b.

The opening 27c formed on the outside of the perforations 22c is configured to expose the projections 24d-24e to be described later of the rubber sponge 20d-20e.

Figure 9D:
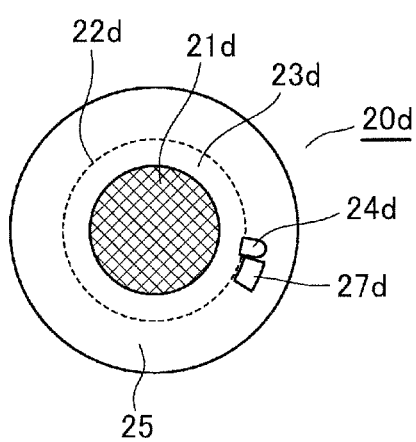
Figure 9E:
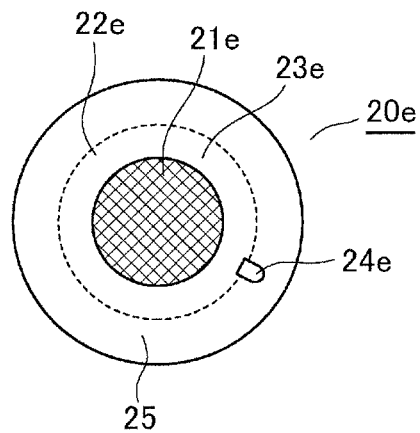

Similarly, in the case of the disposable rubber sponge 20d, as shown in FIG. 9D, the disposable rubber sponge 20d includes a mesh portion 21d having a predetermined size, a circular perforations 22d, and a projection 24d, the circular perforations 22d outside of the mesh portion 21d is positioned outside a position of the perforations 22c of the disposable rubber sponge 20c. Further, in the case of the disposable rubber sponge 20e, as shown in FIG. 9E, the disposable rubber sponge 20d includes a mesh portion 21e having a predetermined size, a circular perforations 22e, and a projection 24e, the circular perforations 22e outside of the mesh portion 21d is positioned outside a position of the perforations 22d of the disposable rubber sponge 20d.

In FIG. 9D, the opening 27d formed on the outside of the perforations 22d is configured to expose the projection 24e to be described later of the rubber sponge 20e.

Figure 10:
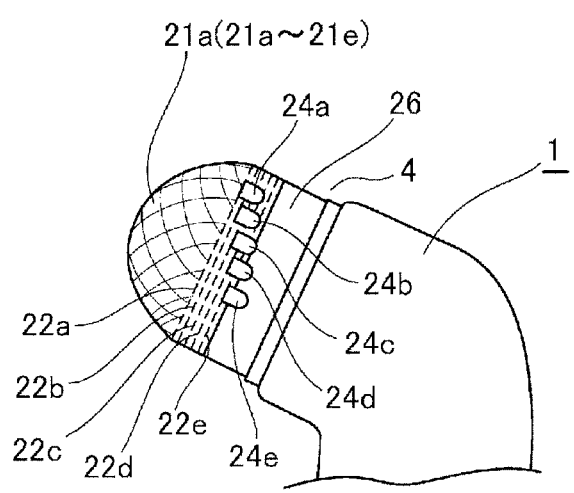
FIG. 10 is a diagram illustrating a state in which the disposable rubber sponge is attached to the rubber sponge attachment portion for use in the second embodiment.

FIG. 10 is a diagram illustrating a state in which disposable rubber sponges 20a-20e are superimposed sequentially, for example, to be attached to the rubber sponge attachment portion 4 by a fastener 26.

In this case, the disposable rubber sponge 20a is positioned at the distal end of the sponge rubber attachment portion 4, for example, and the disposable rubber sponge 20b, 20c, 20d, 20e are disposed sequentially underneath.

Further, in FIG. 10, the opening 27a-27d are omitted to clarify structure of the perforations 22a-22e.

Therefore, in the present embodiment, the disposable rubber sponge 20a located at the top of the four rubber sponge attachment portions is first used, then a user who uses the poultice applicator catches and pull the projections 24a to separate the mesh portion 21a of the disposable rubber sponge 20a along the perforations 22a without removing the fastener 26, hence it is possible to use a new disposable rubber sponge 20b.

In the same way, when the next user uses the poultice applicator, he catches the projections 24b of the disposable rubber sponge 20b to separate the mesh portion 21b of the disposable rubber sponge 20a along the perforations 22b, hence it is possible to use a new disposable rubber sponge 20c.

By separating the mesh portion 21 along the perforations 22b using the projection 24 in the same manner, a new rubber sponge 20 is exposed, and it is possible to prevent from using a rubber sponge touched to the skin of another person, and from pausing on use of the poultice applicator. In particular, in the present embodiment, it is possible to apply a drug with a new disposable rubber sponge 20 without removing the fastener 26. Further, in the case of the present embodiment, because it uses a single fastener 26, it is possible to shorten the length of the four rubber sponge attachment portion 4.

In the above embodiment, a structure is adopted in which the disposable rubber sponges 20a-20e are superimposed sequentially and are attached to the rubber sponge attachment portion 4 by the fastener 26, for example. However, it is possible that five disposable rubber sponges are attached to the fastener 26 by using an attachment means or the like, for example, so as to fasten to the tip of the poultice applicator 1. In this case, first the existing rubber sponge provided in the rubber sponge attachment portion 4 in advance is removed, and then the fastener 26 to which the disposable rubber sponges are attached.

Further, the poultice applicator has the structure that uses five disposable rubber sponges 20a-20e in the above description of the embodiment. However, it is possible that a poultice applicator includes five or more disposable rubber sponges.

Further, each of the disposable rubber sponges 20a-20e has the perforations. However, there is no need to have the perforations if it is possible the rubber sponges 20a-20e are cut along the outer periphery of the fastener 26.

Third Embodiment

Next, a third embodiment according to the present invention will be explained.

The present embodiment discloses a poultice applicator that has a single fastener similar to the second embodiment, but has a disposable rubber sponge that has a different structure from that of the second embodiment. In the following, it will be explained in detail.

Figure 11A:
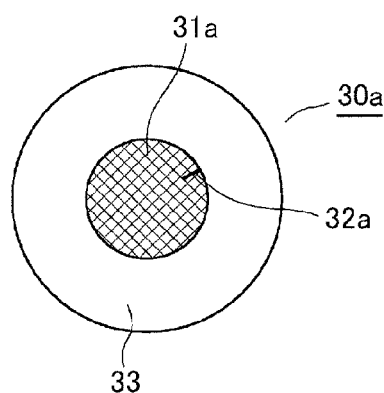
FIG. 11A-11E are diagrams for explaining an example of a disposable rubber sponge to be used in the third embodiment.

FIG. 11A is a diagram illustrating a disposable rubber sponge 30a used in the present embodiment. The disposable rubber sponge 30a includes a mesh portion 31a having a predetermined size at the middle, through which drug contained in the poultice applicator is exuded when the container is pressed. A slit 32a is formed at least a part of the mesh portion 31a. The slit 32a is formed in the diameter direction on the periphery of the mesh portion 31a, as shown in FIG. 11A. For example, the length of the slit 32a is $\frac{1}{5}$ to $\frac{1}{10}$ of the diameter of the mesh portion 31a, and is formed to have a length that does not become the obstacle when applying drug due to its formation at the periphery. In addition, a skirt portion 33 shown in FIG. 11A may be made of a sponge rubber.

Figure 11B:
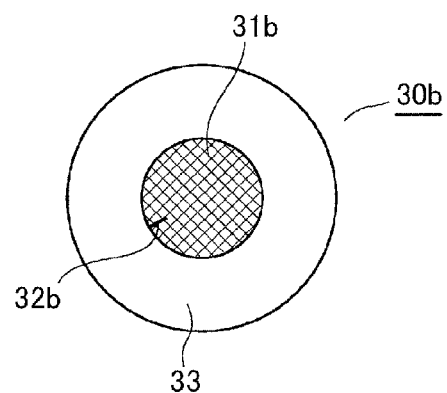

Similarly, FIG. 11B is a diagram illustrating a disposable rubber sponge 30b used in the present embodiment. The disposable rubber sponge 30b includes a mesh portion 31b having a predetermined size at the middle, and a slit 32b is formed at least a part of the mesh portion 31b. The slit 32b, as shown in FIG. 11B, is formed in the diameter direction on the periphery of the mesh portion 31b, and is formed at a position different from the disposable rubber sponge 30a. Specifically, the slit 32a formed at the mesh portion 32a of the rubber sponge 31a is formed at a position different from 180 degree with respect to cuts 32a.

Figure 11C:
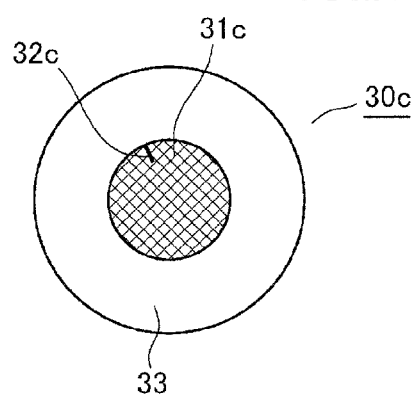

Similarly, FIG. 11C is a diagram illustrating a disposable rubber sponge 30c used in the present embodiment. The disposable rubber sponge 30c includes a mesh portion 31b having a predetermined size at the middle, and a slit 32c is formed at least a part of the mesh portion 31c. The slit 32c, as shown in FIG. 11C, is also formed in the diameter direction on the periphery of the mesh portion 31c, and is formed at a position different from the disposable rubber sponge 30a. Specifically, the slit 32c formed at the mesh portion 31c of the rubber sponge 30c is formed at a position different from 90 degree with respect to cuts 31a and 31b of the mesh portions 32a and 32b.

Figure 11D:
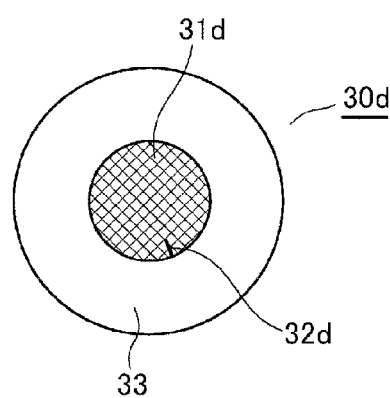

Similarly, FIG. 11D is a diagram illustrating a disposable rubber sponge 30d used in the present embodiment. The disposable rubber sponge 30d includes a mesh portion 31b having a predetermined size at the middle, and a slit 32d is formed at least a part of the mesh portion 31d. The slit 32d, as shown in FIG. 11D, is also formed in the diameter direction on the periphery of the mesh portion 31d, and is formed at a position different from the disposable rubber sponge 30a and the like. Specifically, the slit 32c formed at the mesh portion 32c of the rubber sponge 30c is formed at a position different from 180 degree with respect to cut 31c of the mesh portion 32c.

Figure 11E:
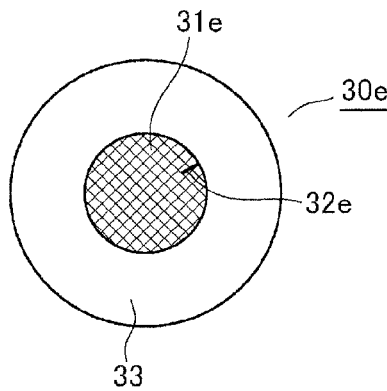

Further, a disposable rubber sponge 30e includes a mesh portion 31e of a predetermined size as shown in FIG. 11E, the mesh portion 31e has a slit 32e formed in a part of the mesh portion 31e, and the position of the slit 32e of the mesh portion 31e is formed at the same position with the slit 32a formed in the mesh portion 32a of the disposable rubber sponge 31a.

Figure 12:
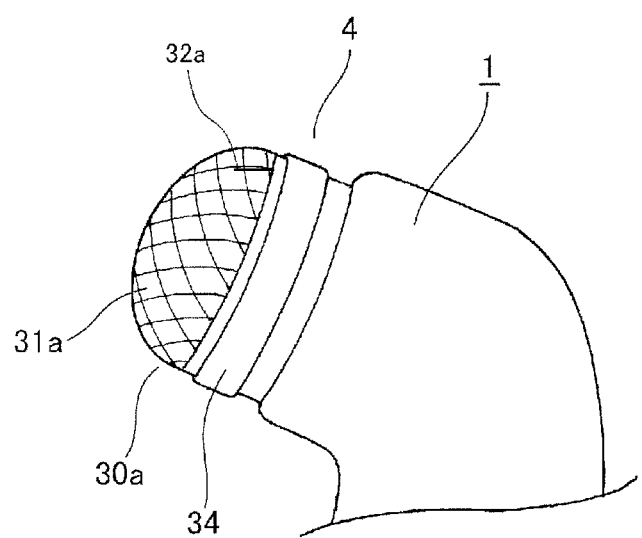
FIG. 12 is a diagram showing a state in which the disposable rubber sponge is attached to the rubber sponge attachment portion for use in the third embodiment.
Figure 13:
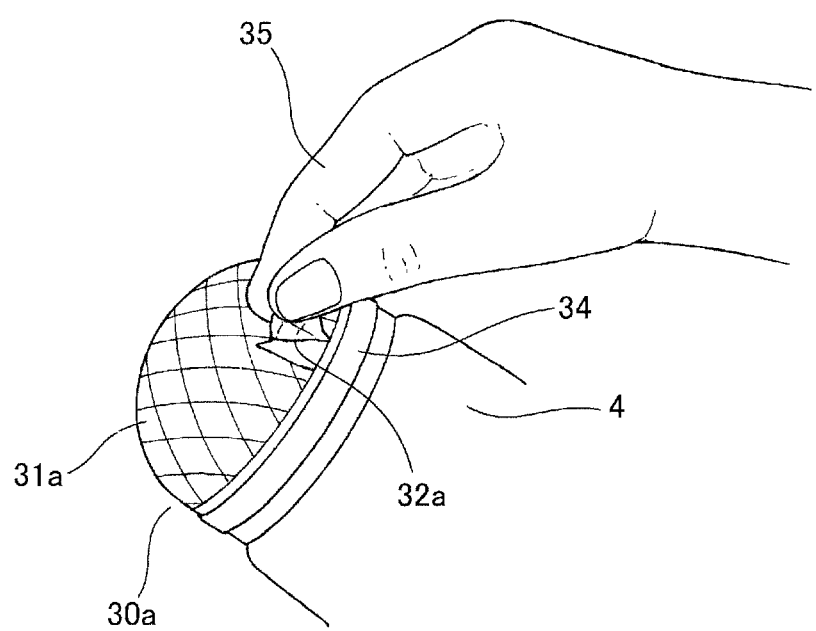
FIG. 13 is a diagram for explaining a state in separating the disposable rubber sponge used in the third embodiment.

FIG. 12 is a diagram illustrating a state in which the disposable rubber sponges 30a-30e of the above configuration are superimposed sequentially to be attached to the rubber sponge attachment portion 4 by a fastener 34, for example. In this case, for example, the disposable rubber sponges 30a is positioned at the tip of the disposable rubber sponges 30a, and the disposable rubber sponge 30b, 30c, 30d, 30e are disposed sequentially underneath. In this state, the disposable rubber sponge 30a located at the top of the four rubber sponges attachment portion is used first, then a user who uses the poultice applicator catches and pulls the projections 32a by their fingers 35 to cut and separate the mesh portion 31a, hence it is possible to expose a underlying mesh portion 31b. Further, the state shown in FIG. 13, the finger 35 of one hand catches and pulls the slit 32a. However, it is possible to separate the mesh portion 31 easily by catching and pulling the both sides of the slit 32a with the fingers of the hands. Further, by forming the mesh portion 31a on the extension line of the slit 32a to be cut easily, mesh portion 31a can be exposed more certainly. For example, it may be possible that a rubber of the mesh portion 31a on the extension line of the slit 32a is configured to be thin.

It is possible that, in this way, the mesh portion 31a is cut and opened, and the mesh portion 31b of the unused (new) disposable rubber sponge 30b is exposed, hence it is possible to apply drug to the skin through the unused (new) disposable rubber sponge 30b.

In the same manner, even when the next user uses the poultice applicator, it is possible that the mesh portion 31b may be cut and opened by using a slit 32b of the disposable rubber sponge 30b and the next person uses a unused (new) disposable rubber sponge 30c. Further, the mesh parts 31a and 30b of the disposable rubber sponge 30a and 30b remain in the tip of the rubber sponge attachment portion 4. However, for example, by pulling a part of the mesh portions 31a, 31b that have been cut and opened, the edge portion of the mesh portion 31a and 31b may be cut along the fastener 34 so that the remained mesh parts 31a and 30b may be separated.

Further, as described in the second embodiment, perforations may be formed outside the mesh portion 32 to separate the remained mesh parts 31a and 30b easily.

Therefore, it is possible to prevent from using a rubber sponge touched to the skin of another person, and from pausing on use of the poultice applicator. In particular, in the present embodiment, it is possible to apply a drug with a new disposable rubber sponge 20 without removing the fastener 34.

Furthermore, in the case of the present embodiment, because it uses a single fastener 26, it is possible to shorten the length of the four rubber sponge attachment portion 4.

In the above embodiment, a structure is adopted in which the disposable rubber sponges 30a-30e are superimposed sequentially and are attached to the rubber sponge attachment portion 4 by the fastener 34, for example. However, it is possible that five disposable rubber sponges are attached to the fastener 34 by using an attachment means or the like, for example, so as to fasten to the tip of the poultice applicator 1. In this case, first the existing rubber sponge provided in the rubber sponge attachment portion 4 in advance is removed, and then the fastener 34 to which the disposable rubber sponges are attached.

Further, the poultice applicator has the structure that uses five disposable rubber sponges 30a-30e in the above description of the embodiment. However, it is possible that a poultice applicator includes five or more disposable rubber sponges.

Fourth Embodiment

Next, a fourth embodiment according to the present invention will be explained.

The present embodiment is intended to improve the fastener 26, 34 used in the second and third embodiments described above. In the following, In the following, it will be explained in detail.

Figure 14A:
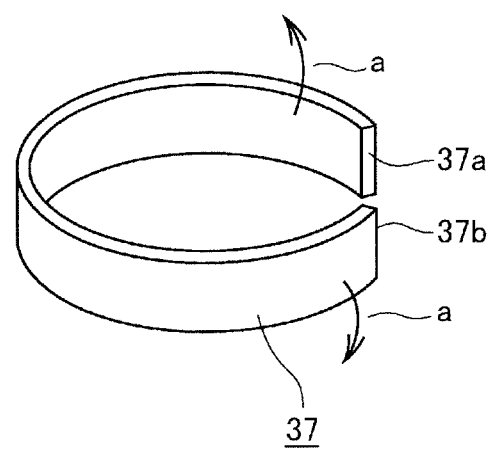
FIGS. 14A and 14B are diagrams for explaining a fourth embodiment and modifications of the fastener.

FIG. 14 is a diagram illustrating a structure of the fastener 37. The fastener 37 has the structure in which a part of the circular fastener 26, 34 is deleted, and the fastener 37 is made of metal, resin or the like. The length between the end portions 37a, 37b of the fastener 37 may be set shorter than the diameter of the rubber sponge attachment portion 4 described above, and the inner diameter of the fastener 37 is set narrower than the outer diameter of the rubber sponge attachment portion 4. Therefore, the disposable rubber sponges 20a-20e, 30a-30e are attached to the rubber sponge attachment portion 4, and the fastener 37 is engaged into the rubber sponge attachment portion 4, then the fastener 37 may be spread in a direction indicated by an arrow a in FIG. 14A.

Hence, the disposable rubber sponge is fitted to the rubber sponge attachment portion 4 by pressing force of the fastener 37.

Figure 14B:
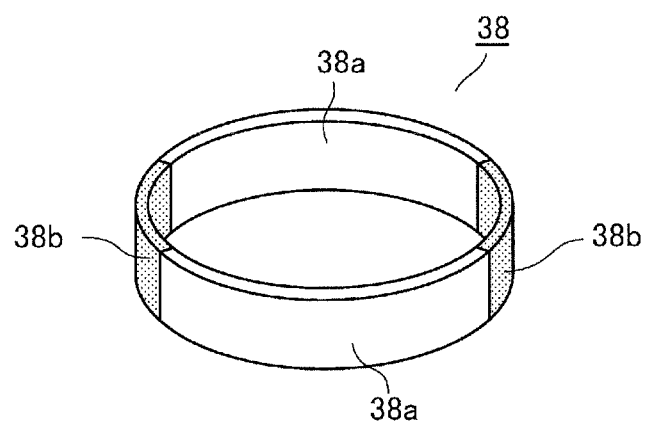

On the other hand, FIG. 14B is a diagram illustrating a configuration of a fastener 38 of a modification of the present embodiment. The fastener 38 has a circular shape and is constituted by a member 38b 38a.

Therefore, similar to the above mentioned case, the disposable rubber sponges 20a-20e, 30a-30e are attached to the rubber sponge attachment portion 4, and the fastener 37 is engaged into the rubber sponge attachment portion 4, then the disposable rubber sponge is fitted to the rubber sponge attachment portion 4 by pressing force of the fastener 38.

Fifth Embodiment

Next, a fifth embodiment according to the present invention will be explained.

In this embodiment, in the basic structure of the poultice applicator 1 in which the analgesic and antiphlogistic poultice 2 is contained, that is, the poultice applicator 1 has the container in which the analgesic and antiphlogistic poultice 2 is contained and the rubber sponge attachment portion 4, antipruritic and anti-inflammatory poultice may be used instead of the analgesic and antiphlogistic poultice 2, as similar to the case of the first embodiment. The poultice applicator 1 according to this embodiment, a structure of the rubber sponge attachment portion 4 may be different from that in the previous embodiments. In the following, it will be explained in detail.

FIG. 15 is a diagram illustrating a configuration of disposable rubber sponge that is used in this embodiment. As shown in FIG. 15, the disposable rubber sponge 14 of the present embodiment has a mesh structure covering the entire surface. For example, elastic member 15 such as a rubber-band is attached to four corners 14' of the disposable rubber sponge 14. Specifically, the elastic member 15 such as a rubber-band may be attached to the four corners 14' of the disposable rubber sponge 14, as shown in an arrow.

Figure 16:
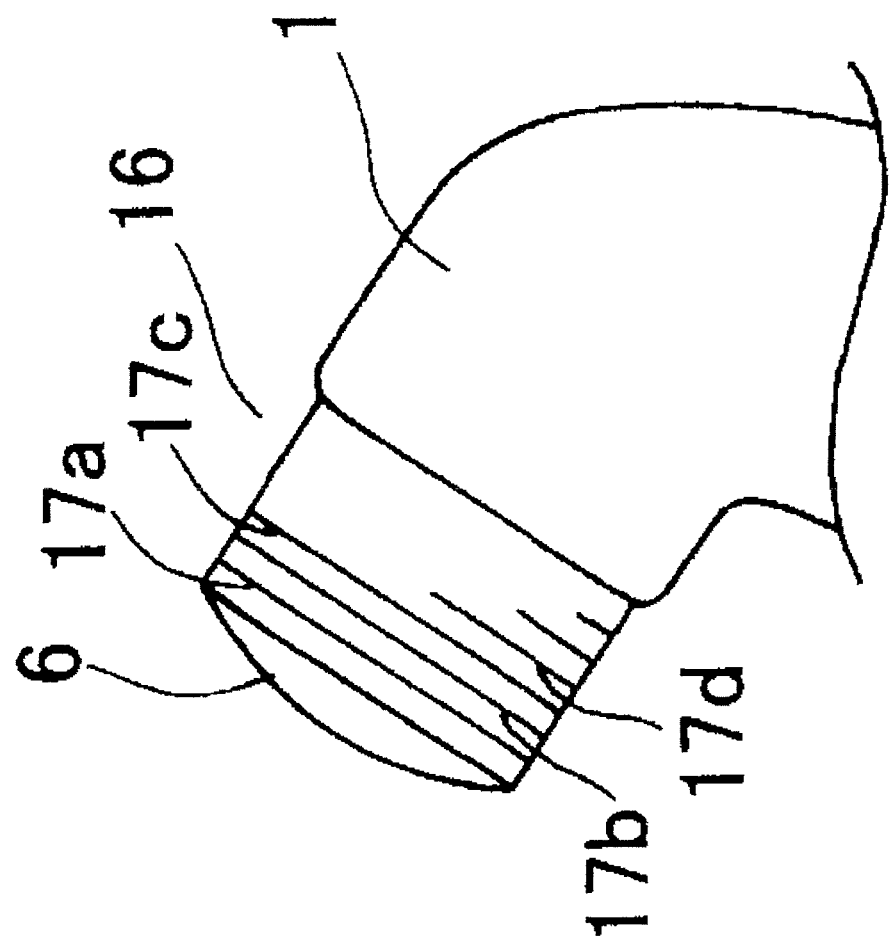
FIG. 16 is a diagram illustrating a state in which disposable rubber sponge of the fifth embodiment is attached to cover the rubber sponge attachment portion by a fastener.

FIG. 16 is a diagram illustrating the structure of a rubber sponge attachment portion 16 and illustrating a state in which no disposable rubber sponge is attached. As describer above, an existing rubber sponge 6 is attached to the tip of the rubber sponge attachment portion 16.

Figure 17:
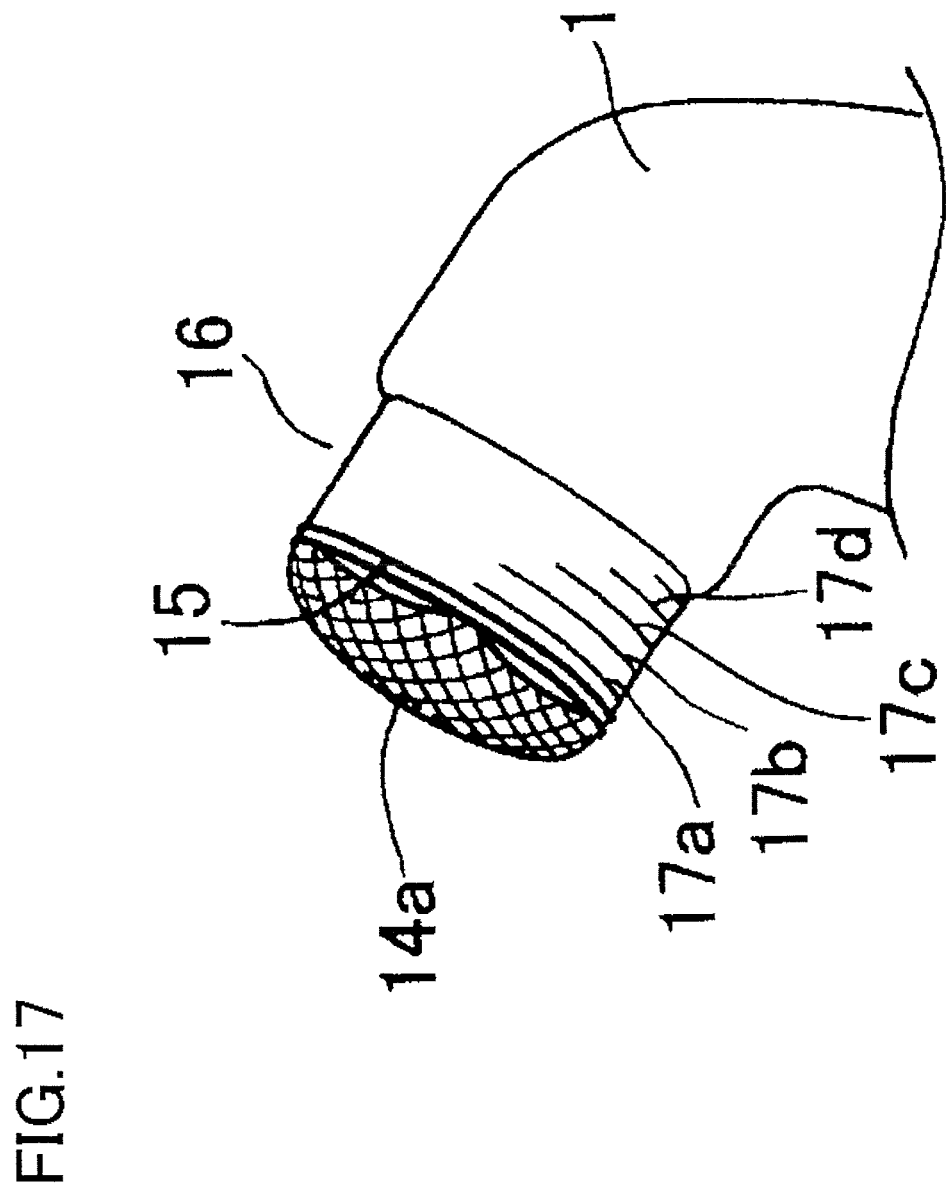
FIG. 17 is a diagram illustrating a state in which a first disposable rubber sponge is attached to cover a disposable rubber sponge.

In this embodiment, in order to use the elastic member 15 such as a rubber-band, grooves 17a, 17b, ..., are formed at regular intervals on the circumference of the rubber sponge attachment portion 16, and the elastic member 15 such as a rubber-band are engaged into the grooves 17a, 17b, ..., FIG. 17 is a diagram illustrating a state in which a first disposable rubber sponge 14a is attached to cover the existing disposable rubber sponge 6, that is, the elastic member 15 such as a rubber-band is engaged in the rubber sponge attachment portion 16.

Although not shown, a second disposable rubber sponge 14b, a third disposable rubber sponge 14c, a third disposable rubber sponge 14c, ..., are attached to the rubber sponge attachment portion 16 sequentially, and each of the elastic members 15 such as rubber-bands may be engaged in the corresponding groove 17a, 17b, ....

Therefore, when using the poultice applicator 1 of the present embodiment, for example, when the four disposable rubber sponges 14a-14d is attached to the poultice applicator 1, the first disposable rubber sponges 15d attached to the rubber sponge attachment portion 16 at the top level is used, and then a next user who uses the poultice applicator 1 removes the elastic member 15 such as rubber-band from the groove 17d to discard the disposable rubber sponge 14d, hence the next user may use a unused (new) disposable rubber sponge 14c to apply drug to the skin.

Similarly, the disposable rubber sponge 14c, 14b, 14a may be used sequentially, and it is possible to prevent from using a rubber sponge touched to the skin of another person, and from pausing on use of the poultice applicator.

Further, the poultice applicator has the structure that uses four disposable rubber sponges 14a-14d in the above description of the embodiment. However, it may be possible that the poultice applicator 1 includes four or more disposable rubber sponges.

It is possible that, for example, in travel or camping, it is not necessary to carry any rubber sponge for replacement due to such configuration of the poultice applicator 1, and it is possible to achieve the poultice applicator 1 that can be used by many users even if the only one poultice applicator 1 is carried.

In the above, the first to fifth embodiments have been described. All of the embodiments has the structure in which the rubber sponge attachment portion 4 is attached to the poultice applicator 1 and the disposable rubber sponge is attached to the rubber sponge attachment portion 4. In the poultice applicator 1, it is not limited to use the sponge, and cloth, resin or the like can be used instead of the sponge.

In this case, for example, synthetic rubber and natural rubber is attached to the rubber sponge mounting portion 4 as the disposable rubber sponge. The synthetic rubber is exemplified as ethylene-propylene rubber and chloroprene rubber, silicone rubber, etc.

Further, when using a cloth, for example, the rubber sponge attachment portion 4 may be the name of a disposable cloth attachment portion. For example, synthetic fibers or natural materials such as cotton, silk, hemp, etc., and a woven fabric as the fabric material can be used without being limited to nonwoven fabric.

Further, when using a cloth, depending on the weave, it is possible that no mesh portion can also be provided. For example, if the required drug is applied without providing a mesh portion, it is not necessary to provide the mesh portion.

It is not limited the rubber sponge attachment portion 4 uses not only thermoplastic resins such as polyamide and polyethylene but also thermosetting resins such as epoxy resin or phenolic resin.

What is claimed is:

1. A poultice applicator in which a drug is to be applied to human skin comprising a container to which an existing rubber sponge, cloth or resin is attached, a plurality of disposable members and a disposable member attachment portion, each of the disposable members comprising a mesh portion having a mesh formed at a middle of the disposable member and having a predetermined size, perforations formed outside of the mesh portion and a projection formed between the mesh portion and the perforations, are superposed sequentially, and are attached to the disposable member attachment portion by a fastener.

2. The poultice applicator according to claim 1, wherein the plurality of disposable members comprises a disposable rubber sponge, cloth or resin, and wherein the disposable rubber sponge, cloth or resin covers the existing rubber sponge, cloth or resin, and is attached to the disposable member attachment portion by the fastener.

* * * * *